United States Patent [19]
Kandler et al.

[11] Patent Number: 5,352,773
[45] Date of Patent: Oct. 4, 1994

[54] STABLE HEMOGLOBIN BASED COMPOSITION AND METHOD TO STORE SAME

[75] Inventors: Richard L. Kandler, McHenry; John C. Spicuzza, Highland Park, both of Ill.

[73] Assignee: Baxter International Inc., Deerfield, Ill.

[21] Appl. No.: 962,623

[22] Filed: Oct. 16, 1992

Related U.S. Application Data

[63] Continuation of Ser. No. 811,887, Dec. 19, 1991, abandoned, which is a continuation of Ser. No. 562,786, Aug. 6, 1990, abandoned.

[51] Int. Cl.$^5$ .............. C07K 13/00; A61K 35/14; A61K 37/00; C07C 103/52
[52] U.S. Cl. .............................................. 530/385
[58] Field of Search ............................. 514/6; 530/385

[56] References Cited

U.S. PATENT DOCUMENTS

| | | |
|---|---|---|
| 3,712,848 | 1/1973 | Casey et al. |
| 3,953,329 | 4/1976 | Updike |
| 4,053,590 | 10/1977 | Bonsen et al. ............ 514/6 |
| 4,516,984 | 5/1985 | Warner et al. |
| 4,568,327 | 2/1986 | Seufert |
| 4,600,531 | 7/1986 | Walder ...................... 530/385 |
| 4,609,383 | 9/1986 | Bonaventura et al. |
| 4,662,904 | 5/1987 | Ryzin et al. |
| 4,761,209 | 8/1988 | Bonaventura et al. |
| 4,777,244 | 10/1988 | Bonhard et al. |
| 4,872,553 | 10/1989 | Suzuki et al. ............ 206/524.4 |

OTHER PUBLICATIONS

DeVenoto, F., "Stability of hemoglobin solution during storage", J. Lab. Clin. Med. vol. 92, No. 6, pp. 946–952 (1978).
Hamilton, P. F., "Preparation of Hemoglobin Solutions for Intravenous Infusion", J. Exp. Med. 86:455–463 (1947).
P. Board et al., *Methaemoglobinaemia Resulting from Heterozygosity for Two NADH-Methaemoglobin Reductase Variants: Characterization as NADH-Ferricyanide Reductase*, 47 Brit J. Haemat. 361 (1981).
Brooks, et al., *The Oxidation of Haemoglobin to Methaemoglobin by Oxygen: II-The Relation Between the Rate of Oxidation and the Partial Pressure of Oxygen*, 118 Proc. Roy. Soc. of London 560 (1935).
Bunn et al., *Hemoglobin Oxidation: Methemoglobin, Methemoglobinemia, and Sulfhemoglobinemia*, 634 (W. B. Saunders, 1986).
DeVenuto, *Stability of Hemoglobin Solution During Extended Storage*, 92 J. Lab. Clin. Med. 946 (1980).

(List continued on next page.)

*Primary Examiner*—Howard E. Schain
*Assistant Examiner*—L. Touzeau
*Attorney, Agent, or Firm*—Kent Barta; Sarah E. Bates; Paul C. Flattery

[57] ABSTRACT

The present invention relates to a stable hemoglobin based composition having sufficiently low levels of methemoglobin to effectively function as an oxygen carrying solution upon administration to a patient made by the process comprising: a) adding an oxygenated or deoxygenated form of said blood substitute to an oxygen impermeable package, and b) storing said container at from between 5° C. to 45° C. for sufficient time to permit the autoreduction of methemoglobin. The stable hemoglobin based composition includes hemoglobin, modified hemoglobin and/or encapsulated hemoglobin. To effectively function as an oxygen carrying solution upon administration to a patient, the stable hemoglobin based solution cannot have greater than about 50% of said hemoglobin based solution in the methemoglobin form but, preferably no more than about 15%. The invention further relates to a method to store a stable oxygen carrying solution according to the above discussed process.

2 Claims, 8 Drawing Sheets

OTHER PUBLICATIONS

H. Dixon, *Gel Filtration of Haemoglobin*, 13 Biochemical Ed. (1985).

E. DiTorio, *Preparation of Derivatives of Ferrous and Ferric Hemoglobin*, 76 Method Enzym. 57 (1981).

A. Levy et al., *Hemoglobin; A Source of Superoxide Radical Under Hypoxic Conditions*, Oxy-Radicals in Molecular Biology and Pathology, (Alan R. Liss, 1988).

S. Morell et al., *Deoxygenation of Hemoglobin in Closed Cuvettes*, 2 Physio. Chem. & Physics 467 (1970).

F. Scheller, et al., *Mechanism of Cathodic Reduction of Hemoproteins*, 60 Studia Biophy Sica Berlin 137 (1976).

L. Stratton et al., *The Reduction of Methemoglobin Levels by Antioxidants*, 12 Hemoglobin 353 (1988).

R. Sprokholt et al., *Quality Control Material Containing Hemoglobin for Blood Gas and pH Measurement: Preparation of Stroma-Free Hemoglobin Solution*, 47 Scand. J. Clin. Lab. Inv. 69–72 (1987).

Paul B. Hamilton et al., *Preparation of Hemoglobin Solutions for Intravenous Infusion*, The United States Navy Research Unit of the Hospital of the Rockefeller Institute for Medical Research, pub. Sep. 3, 1947.

Akira Hayashi et al., *An Enzyme Reduction System for Metmyoglobin and Methemoglobin and its Application to Functional Studies of Oxygen Carriers*, Biochemica et Biophysica Acta, 310 (1973) 309–316.

Donald E. Hultquist, et al., *The Methemoglobin Reduction system of Erythrocytes*, Dept. of Biological Chemistry, The University of Michigan, Ann Arbor, MI 48104.

Akihiko Kajita et al., *A Simple Non–Enzymatic Method to Regenerate Oxyhemoglobin from Methemoglobin*, Biochem. and Biophys. Res. Communications vol. 39, No. 6, 1970.

Joseph A. Watkins et al., *Autoxidation Reactions of Hemoglobin A Free From Other Red Cell Components: A Minimal Mechanism*, Biochem. and Biophys. Research Communications, vol. 132, No. 2, 1085.

Akio Tomoda et al., *Characterization of Intermediate Hemoglobin Produced During Methemoglobin Reduction by Ascorbic Acid*, J. of Biol. Chemistry, vol. 253, No. 20, pp. 7415–7419, 1978.

STABLE HEMOGLOBIN BASED COMPOSITION AND METHOD TO STORE SAME

This is a continuation of application Ser. No. 7/811,887, filed on Dec. 19, 1991, now abandoned, which is a continuation of application Ser. No. 07/562,786, filed on Aug. 6, 1990 also now abandoned.

BACKGROUND OF THE INVENTION

1. Field of the Invention

This invention relates to a stable hemoglobin-based oxygen-carrying composition and methods to store or process same, said hemoglobin composition including hemoglobin, modified hemoglobin and encapsulated hemoglobin.

2. Description of Related Art

Although human whole blood and packed red cell preparations have long been used to restore body oxygen-carrying function, hemoglobin-based compositions are now seen to offer several advantages over these currently standard hemotherapies. Patient safety would be enhanced by eliminating untoward reactions to blood group antigens, improving the maintenance of systemic acid-base and electrolyte balance, and avoiding exposure to blood contaminated with diseases such as AIDS and hepatitis. The high costs of testing blood for blood group antigens and disease factors would also be avoided. Further, hemoglobin-based oxygen-carrying substitutes are expected to have prolonged stability during storage so a more stable supply should be realized.

While a number of parameters may be measured to characterize hemoglobin solution stability, such as oxygen carrying capacity and ionic composition, the most important of these is the oxidation state of hemoglobin iron. The iron atom in each of the heme prosthetic groups of the hemoglobin molecule is the site of oxygen binding and release. In order to maintain this reversible oxygen binding capability, the heme iron must be in the physiological $Fe^{2+}$ state. When a solution of hemoglobin is stored for a long period of time, the iron tends to oxidize to the $Fe^{3+}$ state, giving the methemoglobin form which does not reversibly bind oxygen and is therefore physiologically ineffective. (H. F. Bunn et al. Hemoglobin: Molecular Genetic and Clinical Aspects 640 (1986)).

One current strategy to prevent the above described hemoglobin autoxidation reaction is the addition of anti-oxidants (Stratton, L. P., Hemoglobin 12(4):353–368(1988)) such as NADH (Kajita, A. et al., Biochem. Biophys. Res. Comm. 39:1199(1970)). However, in hemoglobin solutions some anti-oxidants can become pro-oxidants (ibid. Stratton et al.). Further, the addition of a component to an intravenous solution product complicates manufacture and raises issues of the toxicity of the new component which can require costly testing during development.

The active reduction of methemoglobin in solution can be accomplished by electrochemical means (P. Scheller, Mechanism of Cathodic Reduction of Hemoproteins, 60 Studia Biophysica 137 (Berlin) (1976)), the use of reductive enzyme systems (Hayashi, A. et al. Biochem. Biophys. Acta 310:309(1973)) or the addition of chemical reducing agents such as ascorbate (Tomoda, A. et al., J. Biol. Chem. 253 (20):7415–7419 (1978)). These systems all require chemical additives and suffer from the same limitations mentioned above for anti-oxidants.

A viable hemoglobin based oxygen-carrying composition should contain less than 50% and preferably less than 15% methemoglobin over the shelf life. The rate of hemoglobin auto-oxidation is, of course, dependent on temperature. Thus, at room temperature (25° C.) heme iron oxidation can exceed 30% per day (See Devenuto, F., infra at 946). Consequently, hemoglobin based oxygen carrying compositions are typically stored in the frozen state to obtain the targeted shelf-life.

The extent of hemoglobin protein purity is an important consideration in any discussion of hemoglobin stability in solution. Hemoglobin heme iron is continuously oxidized in vivo and the red cell contains enzyme systems that directly reduce methemoglobin to restore hemoglobin function. (Hultquist, D. E. et al., The Methemoglobin Reduction System of Erythrocytes, in The International Conference on Red Cell Metabolism and Function, 297–301; Univ. of Michigan (1974)). Paul, H. B. et al, Preparation of Hemoglobin Solutions for Intraveneous Infusions, 455, 463 (1947). Other red cell enzymes eliminate activated oxygen products, such as superoxide and hydrogen peroxide, that can also oxidize heme iron. (Watkins J. A. et al., Biochem. Biophys. Res. Comm. 132(2):742–748 (1985)). It is not surprising therefore that less pure preparations of hemoglobin exhibit increased oxidation stability, particularly when the native methemoglobin reductase substrates, such as NADH, are added to the preparation (Stratton, L. P. et al., Hemoglobin 12(4):353–368 (1988)). Despite this oxidative protection in impure preparations, contaminating proteins can cause immunogenic reactions in patients or may possess innate toxic properties when free in the circulation. Thus, a system that could provide oxidation stability and/or reduce methemoglobin in purified hemoglobin preparations, over a broad temperature range, would possess a substantial advantage.

SUMMARY OF THE INVENTION

This invention relates to methods to obtain a set of conditions as delineated below, that allow the expression of a hemoglobin autoreduction reaction that spontaneously converts methemoglobin to deoxyhemoglobin in purified hemoglobin preparations. This autoreduction reaction is accelerated at higher temperatures, and as long as the proper conditions are maintained as delineated below, the system provides oxidation stability at room temperature.

The present invention relates to a purified hemoglobin based composition having sufficiently low levels of methemoglobin to effectively function as an oxygen-carrying composition upon administration to a patient. The composition is made by a process comprising: a) adding a purified hemoglobin based oxygen-carrying composition to a substantially oxygen impermeable container, b) storing said container at from between 5° C. to 45° C. for sufficient time to permit autoreduction of methemoglobin, and c) storing said container at a final storage temperature between −270° C. and 45° C. The purified hemoglobin based composition includes hemoglobin, modified hemoglobin and/or encapsulated hemoglobin preparations that have been purified. Purification can be according to any known standard method such as heat treatment. (See Estep, U.S. Pat. Nos. 4,861,867 and 4,831,012 (incorporated by reference)). To effectively restore body oxygen-carrying function, it is presently believed that a stable hemoglobin based composition cannot have greater than about 50%, and preferably less than 15%, of the composition in the methemoglobin form.

It is an object of this invention to be able to store a stable hemoglobin based composition over a wide temperature range.

It is further an object of this invention to stop methemoglobin production and in fact cause $Fe^{3+}$ methemoglobin to convert to reduced $Fe^{2+}$ hemoglobin in said composition.

It is further an object of this invention to store a purified hemoglobin based composition in a system that either substantially excludes and/or actively scavenges oxygen, thus allowing the autoreduction reaction to predominate over autoxidation.

It is still another object of this invention to provide a system of oxygen removal that does not require pretreatment or entry into the storage system. The hemoglobin solution, which may contain an amount of methemoglobin, is stored in a container that is substantially impermeable to oxygen. In this substantially impermeable oxygen environment the hemoglobin autoxidation reaction will consume any oxygen in solution, deoxygenate the remaining $Fe^{2+}$ hemoglobin and allow autoreduction of any methemoglobin to proceed.

It is still another object of this invention to store a purified hemoglobin based composition in the oxygenated form and allow deoxygenation in the container to permit autoreduction.

It is still another object of the system to salvage batches of purified hemoglobin based composition in which unacceptable levels of oxidation have occurred. In this case the purified hemoglobin based composition could be stored in bulk in a substantially impermeable container.

It is still another object of this invention to store the deoxygenated, purified hemoglobin based composition in any system which allows diffusion of oxygen from the solution into an area surrounding the container but not outside a substantially oxygen impermeable outer container.

BRIEF DESCRIPTION OF DRAWINGS

For a fuller understanding of the nature and objects of the invention, reference should be made to the following detailed description taken in connection with the accompanying description forming a part of this specification.

DETAILED DESCRIPTION OF THE INVENTION-BEST MODE

We have observed that in deoxygenated solutions of purified hemoglobin, oxidized $Fe^{3+}$ methemoglobin heme iron will spontaneously reduce to the physiologically useful $Fe^{2+}$ form. Based on this discovery we have developed a packaging and storage system that allows the expression of the autoreduction reaction.

The components necessary to perform the packaging operation are sealed in an isolator (glove chamber). These components would include, for example, plastic bag primary containers for the hemoglobin solution, outer wrap secondary containers that have very low oxygen permeability, pumps, clamps, tubing assemblies, a solution reservoir, and oxygen monitors. The isolator interior is sterilized with a vaporized sterilant such as $H_2O_2$ and then cleared of residual sterilant with low-oxygen grade nitrogen. Oxygen is then rigorously removed from the isolator by carefully purging the isolator interior and all components within it with nitrogen. Preferably, at this stage ultra-pure grade nitrogen would be used with in-line oxygen traps to attain very low oxygen levels.

In the now low oxygen environment of the isolator, the plastic primary containers are filled with aliquots of a thoroughly deoxygenated hemoglobin solution and then sealed in foil pouch secondary containers. When this operation is completed the isolator is opened and the containers are placed in storage.

Although autoreduction has been observed to take place during the deoxygenation of the hemoglobin solution, and can be taken advantage of in this way, the reaction proceeds readily during storage in a substantially oxygen impermeable package and requires no further attention.

After hemoglobin solutions are prepared and packaged as described above, there is typically a period of two to five days before the onset of autoreduction. During this time residual oxygen is scavenged from the solution by the oxidation reaction. Consequently, this oxygen scavenging phase is characterized by either an increase in methemoglobin or, if deoxygenation of the solution and packaging components was rigorous enough, a time during which methemoglobin remains at the initial level. The latter case occurs when oxygen has been reduced to a level at which the rates of autoxidation and autoreduction are equal. The duration of this oxygen scavenging phase is temperature dependent, ranging from less than one day at 45° C. to months at 5° C.

After the oxygen scavenging phase the methemoglobin level begins to decrease and this trend continues in an essentially linear manner to a minimum, generally less than 5% methemoglobin, that is maintained as long as oxygen is substantially excluded.

The acceptable temperature range for reducing methemoglobin in a purified hemoglobin composition during storage is between 5° C., where the autoreduction reaction is very slow, to less than 45° C. above which other degradant reactions can limit shelf-life. Room temperature oxidation stability is achieved with this system. Among the examples below, ongoing experiments are described in which, subsequent to the oxygen-scavenging phase, methemoglobin has been maintained at less than three percent for 231 days at 25° C.

It should be noted that once methemoglobin concentration is sufficiently low to allow said hemoglobin solution to effectively function as an oxygen carrying solution the solution can be stored at from between −270° C. to 45° C.

EXAMPLE 1

In this experiment a dilute solution of a alpha-alpha cross-linked hemoglobin was sealed in screw-capped cuvettes and kept at 25° C. With a dilute solution (approximately 39 μM diaspirin cross-linked hemoglobin) in a cuvette it was possible to noninvasively observe changes in the concentrations of oxy-, deoxy-, met- and total hemoglobin during storage using a standard three-wavelength spectrophotometric method taking measurement at 560, 576 and 630 nm.

All manipulations to prepare samples were carried out in a glove-bag continuously purged with ultra-pure nitrogen. One liter of a dilute solution of purified diaspirin cross-linked hemoglobin in lactated Ringer's solution was deoxygenated by recirculation through a membrane oxygenator charged with ultra-pure nitrogen. The deoxygenated diaspirin cross-linked hemoglobin solution was sealed in screw-capped cuvettes which were stored at 25° C.

Despite the efforts to exclude oxygen, the sample initially contained 20% oxy diaspirin cross-linked hemoglobin, 5.5% met- and 73.7% deoxy diaspirin cross-linked hemoglobin. At five days no detectable oxy diaspirin cross-linked hemoglobin was present and the methemoglobin had risen to 32.5%. The balance was in the deoxy state and total hemoglobin was unchanged (Table 1). These results illustrate the deoxygenation of a hemoglobin solution by the oxidation reaction during the oxygen scavenging phase.

Figure 1:
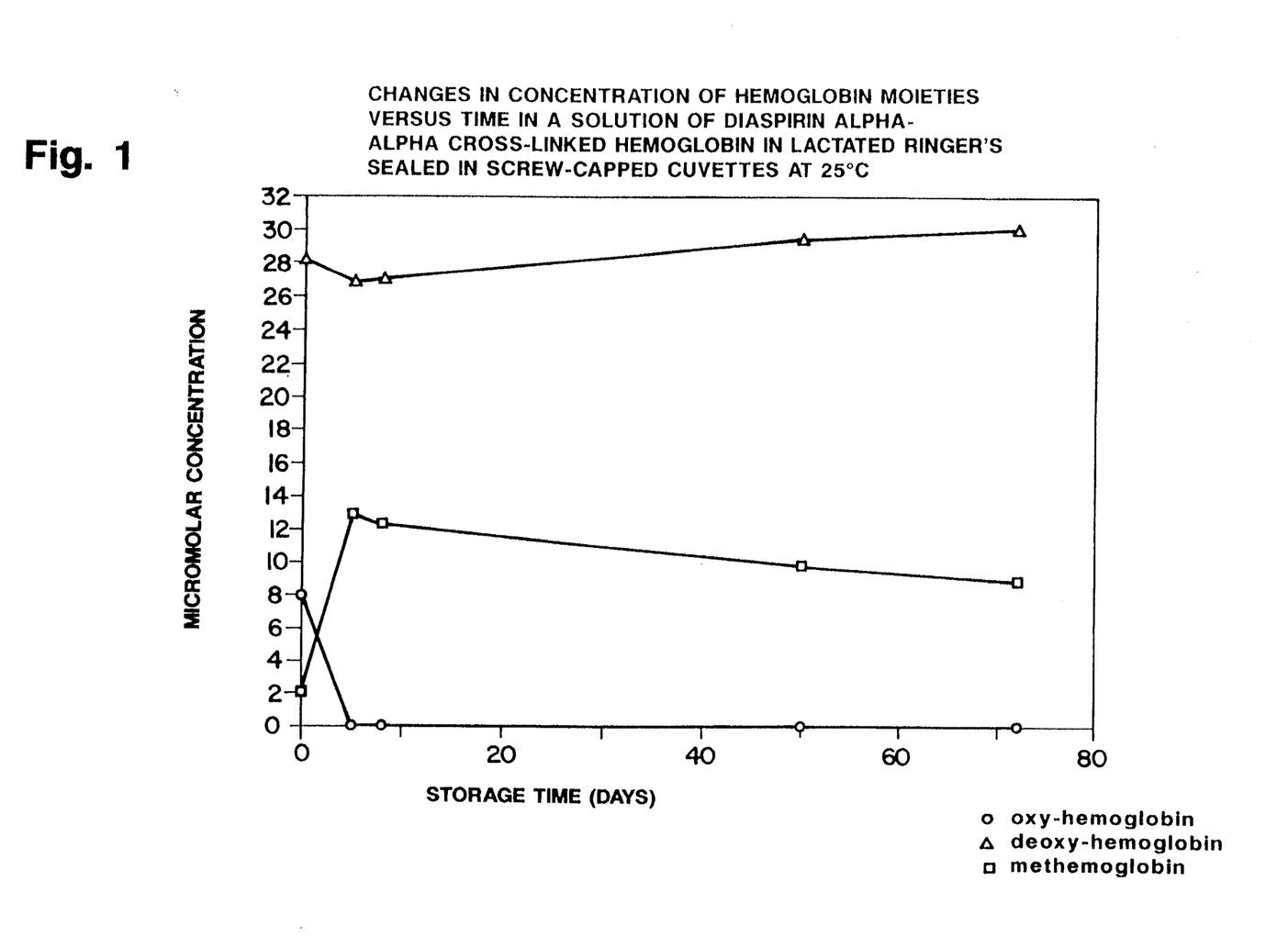
FIG. 1 shows the changes in concentration of hemoglobin moieties versus time in a solution of diaspirin alpha-alpha cross-linked hemoglobin in lactated Ringer's (total diaspirin cross-linked hemoglobin concentration of approximately 39 $\mu M$) that was sealed in a screw-topped cuvette (no head-space) and kept at 25° C.

In subsequent measurements at days 8, 50 and 72 the methemoglobin steadily decreased. See FIG. 1. It is important to observe the actual concentration changes of all three hemoglobin forms and total hemoglobin during the autoreduction rather than percent changes. If methemoglobin were precipitating the percent of that component and the total hemoglobin concentration would fall. The concentration data in Table 1, show the essentially quantitative autoreduction of methemoglobin to deoxyhemoglobin while the total concentration of diaspirin cross-linked hemoglobin remained constant.

TABLE 1

Changes in Percent Content and Micromolar Concentrations of Hemoglobin Moieties in a Solution of Diaspirin Cross-Linked Hemoglobin in Lactated Ringer's Sealed in a Cuvette at 25° C.

| DAY | PERCENT OF TOTAL DIASPIRIN CROSS-LINKED HEMOGLOBIN | | | MICROMOLAR CONCENTRATION | | |
|---|---|---|---|---|---|---|
| | met | oxy | deoxy | met | oxy | deoxy |
| 0 | 5.5 | 20.8 | 73.7 | 2.1 | 8.0 | 28.2 |
| 5 | 32.5 | ND | 67.8 | 12.9 | ND | 26.9 |
| 8 | 31.5 | ND | 68.9 | 12.3 | ND | 27.0 |
| 50 | 25.1 | ND | 75.6 | 9.8 | ND | 29.4 |
| 72 | 23.0 | ND | 77.9 | 8.9 | ND | 30.1 |

ND = not detected.

EXAMPLE 2

In this experiment, efforts were taken to ensure that the samples were stored in sufficiently oxygen impermeable containers to observe autoreduction and obtain an estimate of experimental error in these studies. A dilute solution of diaspirin cross-linked hemoglobin in lactated Ringer's was prepared and deoxygenated as described in Example 1.

Figure 2:
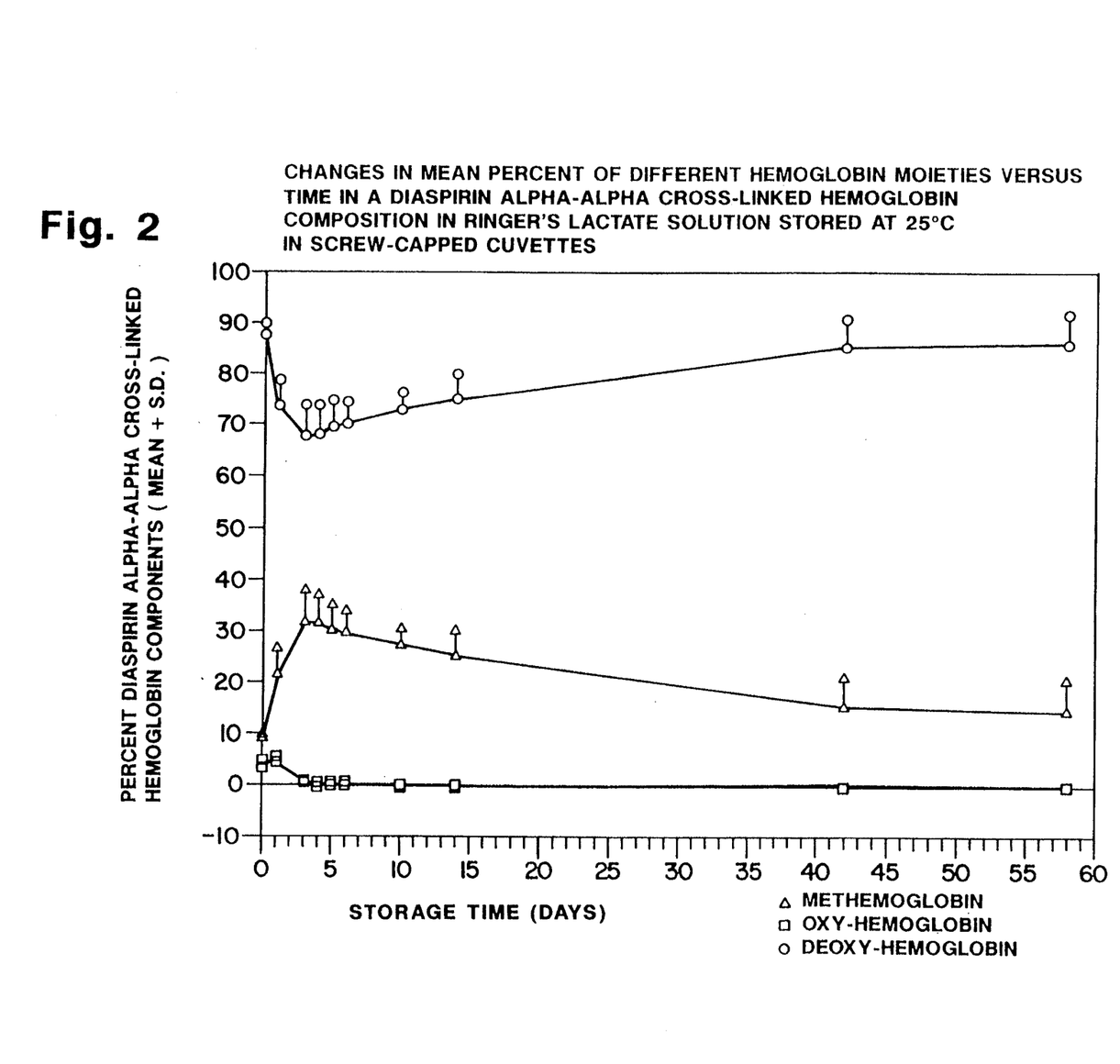
FIG. 2 shows changes in mean percent hemoglobin moieties versus time in sealed screw-capped cuvettes (N=4) that were filled completely with a deoxygenated solution of diaspirin cross-linked hemoglobin in lactated Ringer's (total diaspirin cross-linked hemoglobin concentration of approximately 38$\mu$) and kept at 25° C.

Although an increase in the oxyhemoglobin derivative on day one (FIG. 2, Table 2) indicated oxygen leaks, the results obtained in Example 1 with respect to the quantitative conversion of $Fe^{3+}$ methemoglobin to $Fe^{2+}$ deoxyhemoglobin were reproduced in the four samples prepared within a reasonable degree of precision (see+ S.D. bars in FIG. 2). The mean values of the percent content and micromolar concentrations of the hemoglobin moieties in the sealed cuvettes (N=4) are given in Table 2.

TABLE 2

Changes in Mean Percent of Total Diaspirin Cross-Linked Hemoglobin and Micromolar Concentration of Hemoglobin Moieties at 25° C. in Screw-Capped Cuvettes Containing a Solution of Diaspirin Cross-Linked Hemoglobin in Lactated Ringer's

| DAY | PERCENT OF TOTAL DIASPIRIN CROSS-LINKED HEMOGLOBIN | | | MICROMOLAR CONCENTRATION | | |
|---|---|---|---|---|---|---|
| | met | oxy | deoxy | met | oxy | deoxy |
| 0 | 8.8 | 3.3 | 87.9 | 2.4 | 0.9 | 23.6 |
| 1 | 21.6 | 4.5 | 73.9 | 6.0 | 1.3 | 20.4 |
| 3 | 31.8 | 0.5 | 67.7 | 8.9 | 0.1 | 18.9 |
| 4 | 31.8 | 0.2 | 68.2 | 8.8 | 0.1 | 19.1 |
| 5 | 30.3 | 0.1 | 69.6 | 8.4 | 0.0 | 19.3 |
| 6 | 29.8 | 0.1 | 70.1 | 8.4 | 0.0 | 19.6 |
| 10 | 27.5 | ND | 72.8 | 7.8 | ND | 20.7 |
| 14 | 25.5 | ND | 74.9 | 7.2 | ND | 21.1 |
| 42 | 15.4 | ND | 85.2 | 4.4 | ND | 24.0 |
| 58 | 14.5 | ND | 86.1 | 4.2 | ND | 24.5 |

ND = not detected.

EXAMPLE 3

In the previous examples of the autoreduction reaction in oxygen impermeable systems the diaspirin cross-linked hemoglobin was in a lactated Ringer's medium. To ensure that the observed autoreduction effect was not due to a component in the lactated Ringer's, diaspirin cross-linked hemoglobin was exchanged into phosphate ($PO_4$) buffer. Twenty ml of 10 g/dl diaspirin cross-linked hemoglobin in lactated Ringer's was diluted to one liter with 10 mM $PO_4$; pH=7.40. This fifty-fold dilution was a 98% change of medium. This diluted solution was diafiltered vs. five liters of the same phosphate buffer to effect a further theoretical 99% change in composition of the buffer to phosphate buffer.

Figure 3:
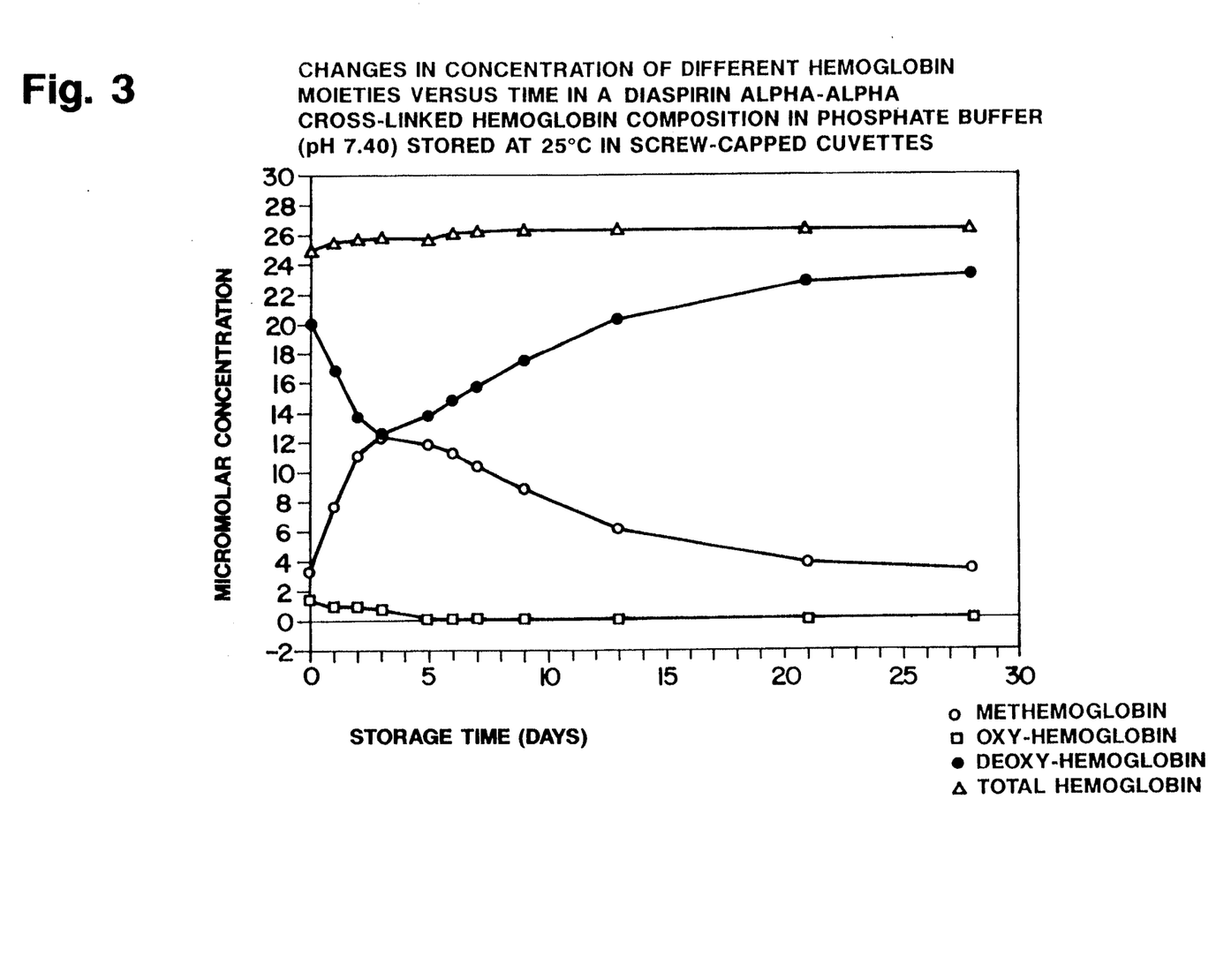
FIG. 3 shows the changes in hemoglobin moieties and total hemoglobin versus time in a deoxygenated solution of diaspirin cross-linked hemoglobin in 10 mM phosphate buffer that was sealed in a screw-capped cuvette (no head space) and kept at 25° C.

This solution of diaspirin cross-linked hemoglobin in phosphate was deoxygenated and a number of screw-capped cuvettes were filled, and sealed as described in Example 1. The characteristic pattern of oxidation followed by autoreduction was observed at faster oxidation and reduction rates relative to Examples 1 and 2. The data from one representative cuvette are given in Table 3 and FIG. 3. The methemoglobin level fell 36.5% (9.3 μM) in twenty-five days.

TABLE 3

Changes in Percent Content and Micromolar Concentration of Hemoglobin Moieties at 25° C. in Screw-Capped Cuvette Containing Diaspirin Cross-Linked Hemoglobin in Phosphate Buffer

| DAY | PERCENT OF TOTAL DIASPIRIN CROSS-LINKED HEMOGLOBIN | | | MICROMOLAR CONCEN-TRATION | | | Total Deoxy Hemoglobin |
|---|---|---|---|---|---|---|---|
| | met | oxy | deoxy | met | oxy | deoxy | |
| 0 | 13.5 | 5.7 | 80.8 | 3.4 | 1.4 | 20.1 | 24.9 |
| 1 | 30.0 | 4.0 | 65.9 | 7.7 | 1.0 | 16.8 | 25.5 |
| 2 | 42.9 | 3.8 | 53.3 | 11.0 | 1.0 | 13.7 | 25.7 |
| 3 | 48.6 | 3.0 | 48.4 | 12.5 | 0.8 | 12.5 | 25.8 |
| 5 | 45.9 | 0.5 | 53.5 | 11.8 | 0.1 | 13.8 | 25.7 |
| 6 | 43.2 | 0.3 | 56.4 | 11.3 | 0.1 | 14.7 | 26.1 |
| 7 | 39.7 | 0.3 | 60.0 | 10.4 | 0.1 | 15.7 | 26.2 |
| 9 | 33.6 | 0.0 | 66.4 | 8.8 | ND | 17.4 | 26.2 |
| 13 | 23.1 | ND | 77.1 | 6.1 | ND | 20.2 | 26.3 |
| 21 | 14.1 | ND | 86.5 | 3.7 | ND | 22.6 | 26.3 |
| 28 | 12.1 | ND | 88.2 | 3.2 | ND | 23.0 | 26.3 |

ND = not detected.

EXAMPLE 4

Figure 4:
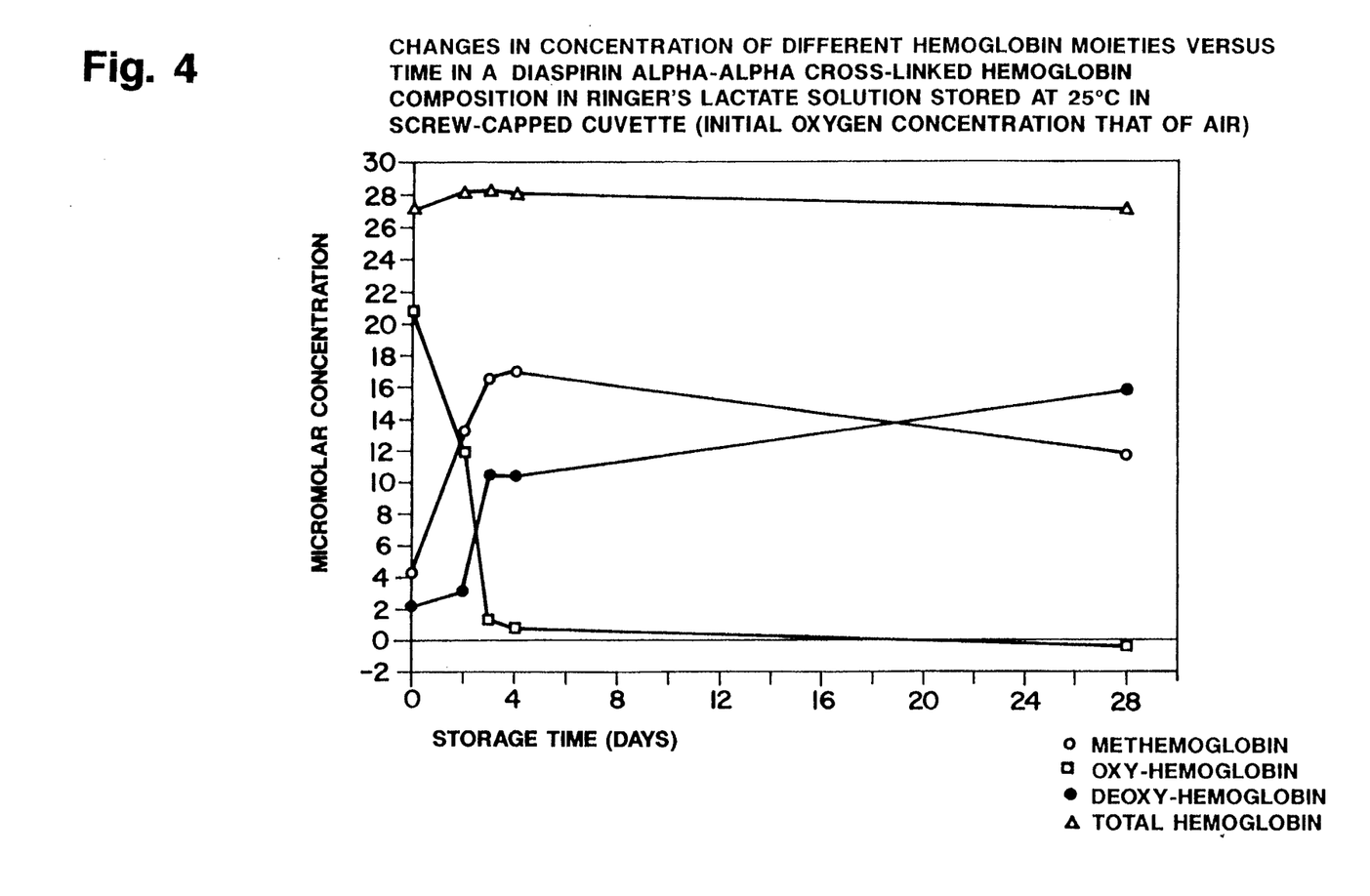
FIG. 4 shows the changes in hemoglobin moieties and total hemoglobin versus time in a solution of diaspirin cross-linked hemoglobin in lactated Ringer's that was equilibrated with air and sealed in a screw-capped cuvette with no head space and kept at 25° C.

The results of this experiment showed that a solution of hemoglobin with a high initial oxygen content would, over a period of time, oxidatively deoxygenate and begin spontaneous autoreduction. A solution of diaspirin cross-linked hemoglobin (27 μM) in lactated Ringer's was sealed in a cuvette with no head space and kept at 25° C. After oxidizing to greater than 60% methemoglobin in four days and concurrently deoxygenating the solution, only 43.1% methemoglobin was present, with no detectable oxy- form, at a day twenty-eight measurement (Table 4; FIG. 4). Although the experiment was not carried any further, it is anticipated that the desired less than 15% methemoglobin level would have been achieved.

TABLE 4

Changes in Percent Content and Micromolar Concentrations of Hemoglobin Moieties at 25° C. in a Sealed Cuvette Containing Undeoxygenated Diaspirin Cross-Linked Hemoglobin in Lactated Ringer's

| DAY | met | oxy | deoxy | met | oxy | deoxy |
|---|---|---|---|---|---|---|
| 0 | 1.6 | 76.4 | 8.0 | 4.2 | 20.8 | 2.2 |
| 2 | 47.1 | 42.0 | 10.9 | 13.3 | 11.8 | 3.1 |
| 3 | 58.5 | 4.4 | 37.0 | 16.6 | 1.2 | 10.5 |
| 4 | 60.4 | 2.6 | 37.0 | 17.0 | 0.7 | 10.4 |
| 28 | 43.1 | ND | 58.3 | 11.7 | ND | 15.8 |

ND = not detected.

EXAMPLE 5

The previous examples demonstrate that spontaneous autoreduction occurs with dilute hemoglobin solutions (approximately 40 μM; 0.29 g/dl of hemoglobin) stored in oxygen impermeable containers. In this experiment we assessed when autoreduction would occur using a concentrated hemoglobin solution (10 g/dl).

All the experimental components necessary to deoxygenate and package the diaspirin cross-linked hemoglobin solution were assembled in a gloved isolator chamber. The isolator was sealed and purged with low-oxygen grade nitrogen to 0.017 ppm oxygen. The 10 g/dl diaspirin cross-linked hemoglobin solution was deoxygenated to two percent oxygen. The test group flexible containers (150 ml internal volume) were filled with approximately 50 ml of deoxygenated diaspirin cross-linked hemoglobin each and then sealed in substantially oxygen impermeable foil pouches.

Two groups of control units were filled under ambient oxygen conditions so the hemoglobin was equilibrated with air oxygen. One group of control units (Ambient Pouched) was sealed in foil pouches and the other (Ambient Not Pouched) was not sealed in a foil pouch. All units were stored in a 25° C. incubator.

At intervals, duplicate packages were pulled from each group and samples were taken from each flexible container with syringe and needle. Aliquots of the 10 g/dl samples were filtered, diluted 50 X in phosphate buffer and spectrophotometrically analyzed for methemoglobin content.

Figure 5:
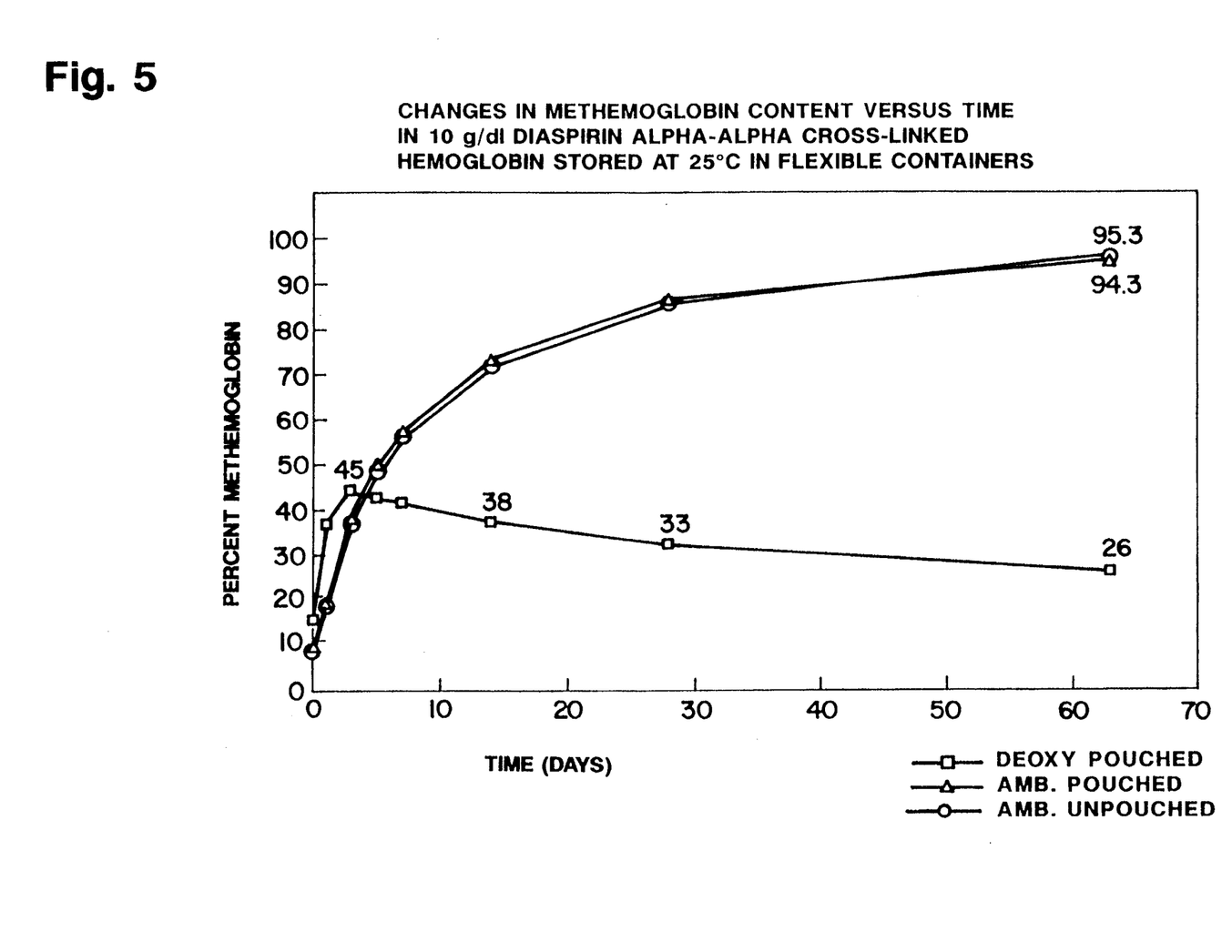
FIG. 5 shows the changes in percent methemoglobin versus time in a solution of 10 g/dl diaspirin cross-linked hemoglobin in lactated Ringer's. The control group units were not deoxygenated and were either sealed in foil pouches (Ambient Pouched) or not (Ambient Not Pouched). All units were kept at 25° C.

After an initial three day oxidation phase, spontaneous autoreduction of methemoglobin was evident in the deoxygenated test group. Over the next sixty days the methemoglobin fell 17.7% in the deoxygenated solution while the oxygenated control group solutions continued to oxidize unabated to over ninety percent methemoglobin (Table 5; FIG. 5). Although the experiment was terminated after 63 days, it would be anticipated that the 15% methemoglobin level preferred for an oxygen-carrying solution would have been reached.

TABLE 5

Changes in Percent Methemoglobin Content in 10 g/dl Solutions of Diaspirin Cross-Linked Hemoglobin in Lactated Ringer's Packaged In Flexible Containers

| TIME/ DAYS | PERCENT METHEMOGLOBIN | | |
|---|---|---|---|
| | DEOXYGENATED TEST GROUP | OXYGENATED CONTROL GROUPS | |
| | | Pouched | Not Pouched |
| PRE* | 8.9 | 8.9 | 8.9 |
| POST** | 15.5 | 8.9 | 8.9 |
| 1 | 36.6 | 19.9 | 18.4 |
| 3 | 43.9 | 38.4 | 36.9 |
| 5 | 42.5 | 50.3 | 48.3 |
| 7 | 41.4 | 57.6 | 56.1 |
| 14 | 37.2 | 73.5 | 71.7 |

TABLE 5-continued

Changes in Percent Methemoglobin Content in 10 g/dl Solutions of Diaspirin Cross-Linked Hemoglobin in Lactated Ringer's Packaged In Flexible Containers

| | PERCENT METHEMOGLOBIN | | |
|---|---|---|---|
| TIME/ DAYS | DEOXYGENATED TEST GROUP | OXYGENATED CONTROL GROUPS | |
| | | Pouched | Not Pouched |
| 28 | 32.2 | 86.4 | 94.3 |
| 63 | 26.2 | 94.3 | 95.3 |

PRE* = preprocessing; the level of methemoglobin before deoxygenation and packaging.
POST** = post-processing; the level of methemoglobin after deoxygenation and packaging were completed.

EXAMPLE 6

Plastic bags were filled with 50 ml of solution and sealed in foil pouches. The packaging operation was carried out in an isolator continuously purged with ultra-pure nitrogen.

The isolator technology described in Example 5 was again used in this experiment. In this example, however, the isolator was fogged with $H_2O_2$ after sealing to sterilize all components used in the packaging operation and more rigorous efforts were employed to purge oxygen from the isolator, the packaging containers and the hemoglobin solution. After fogging, the isolator was purged with low-$O_2$ grade nitrogen. The purge line was then switched to ultra-pure nitrogen with an in-line oxygen trap and the isolator was purged further. All components were carefully purged with the same ultra-pure nitrogen. Additionally, Ageless (Mitsubishi Chemical Co., Inc.) oxygen absorbing packets were added to certain outer envelopes to further reduce oxygen in the container.

The control group did not receive oxygen absorbing packets. They were stored at 25° C. One or four packets were added to the outer envelopes of the two 25° C. test groups. One packet per container was included in another test group that was stored at 5° C.

Figure 6:
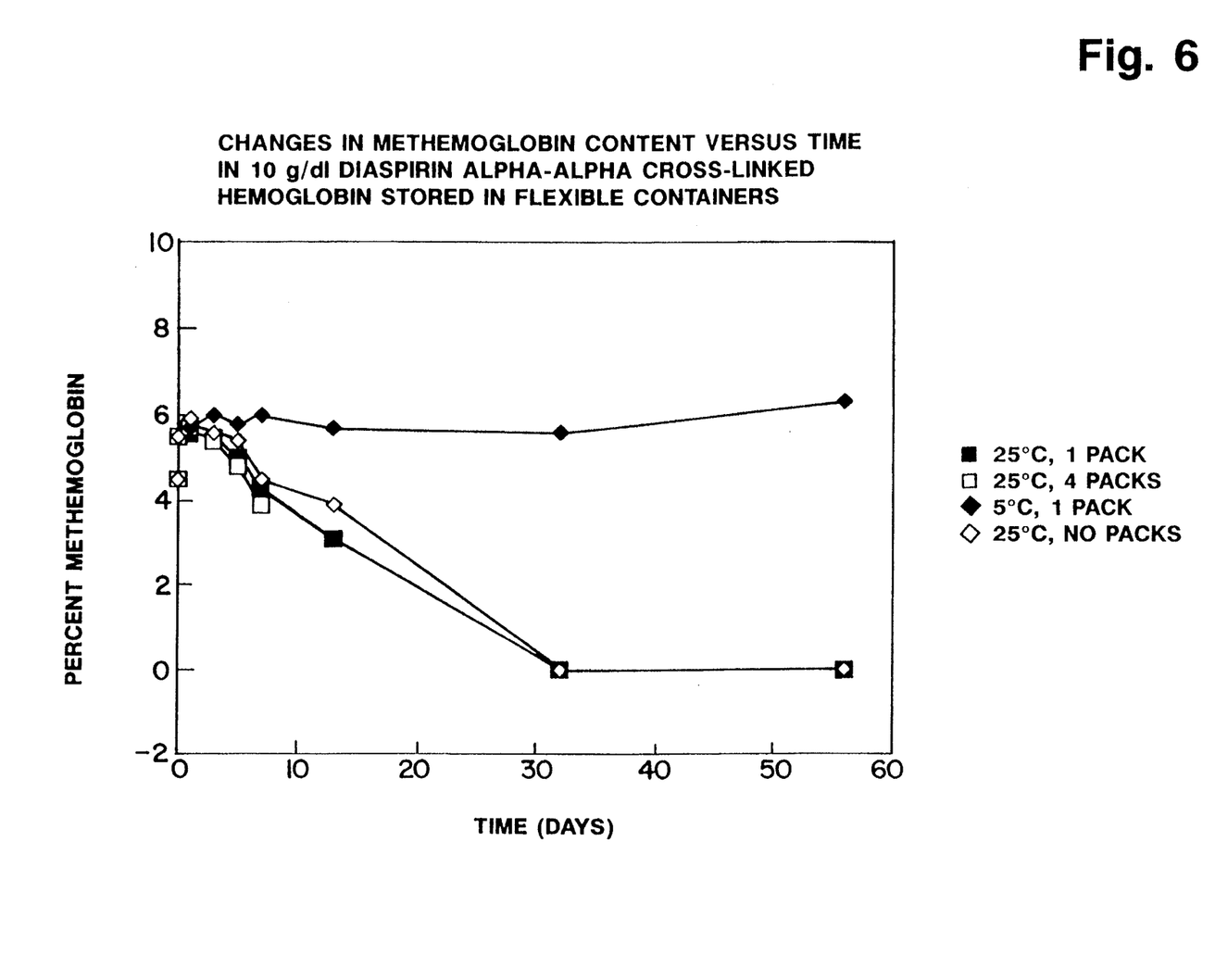
FIG. 6 shows the changes in percent methemoglobin versus time in a deoxygenated solution of 10 g/dl diaspirin cross-linked hemoglobin in lactated Ringer's. Units in the three test groups units were stored at 5° C. with one 100 ml capacity oxygen absorbing packet in the foil pouch, 25° C. with one 100 ml packet or 25° C. with four 100 ml packets. Control group units were stored at 25° C. with no oxygen absorbing packets in the foil pouch.

In contrast to the results observed in Example 5 almost no increase in methemoglobin was observed over the first three days in samples from any of the test or control groups in this experiment. This result indicated that the initial solution oxygen level was sufficiently low to only allow a rate of autoxidation essentially equal to the rate of autoreduction (Table 6; FIG. 6).

Autoreduction was evident on day three in the units from the 25° C. test group containing four oxygen absorbing packets. Methemoglobin could not be detected, after 32 or 56 days, in any units from the 25° C. test group containing one Ageless (Mitsubishi Chemical Co.) packet or the control group. Hemoglobin oxidation continued to day five in the 5° C. stored units and remained at the five day level for the remainder of the study (56 days).

Duplicate samples from each test and control group were submitted for sterility testing and were found to be negative in aerobic and anaerobic culture and did not exceed minimum acceptable pyrogen levels.

TABLE 6

Changes in Percent Methemoglobin Content In 10 g/dl Solutions of Diaspirin Cross-Linked Hemoglobin in Lactated Ringer's Packaged In Flexible Containers

| | PERCENT METHEMOGLOBIN Temp: | | | |
|---|---|---|---|---|
| | 25° C. | 25° C. | 25° C. | 5° C. |
| TIME/ | | # Packets: | | |
| DAYS | 0 | 1 | 4 | 1 |
| PRE* | 4.5 | 4.5 | 4.5 | 4.5 |
| POST** | 5.5 | 5.5 | 5.5 | 5.5 |
| 1 | 5.9 | 5.6 | 5.7 | 5.7 |
| 3 | 5.6 | 5.5 | 5.4 | 6.0 |
| 5 | 5.4 | 5.0 | 4.8 | 5.8 |
| 7 | 4.5 | 4.3 | 3.9 | 6.0 |
| 13 | 3.9 | 3.1 | NS | 5.7 |
| 32 | 0 | 0 | NS | 5.6 |
| 56 | 0 | 0 | NS | 6.3 |

PRE* = preprocessing; the level of methemoglobin before deoxygenation and packaging.
POST** = post-processing; the level of methemoglobin after deoxygenation and packaging were completed.
NS = not sampled.

EXAMPLE 7

The purpose of this experiment was to study the temperature dependence of the hemoglobin oxidation and reduction reactions that take place during storage in the system. Again, a 10 g/dl solution of diaspirin cross-linked hemoglobin in lactated Ringer's was packaged in flexible containers and foil pouches using the isolator technology described in Example 5 and the more rigorous steps to exclude oxygen described in Example 6.

Four groups of test units were packaged, each unit containing one 200 ml capacity oxygen-absorbing packet. The test groups were stored at 5° C., 25° C., 30° C., 45° C. respectively. Control group units were stored at 25° C. without Ageless (Mitsubishi Chemical Co., Inc.) packets. Duplicate samples from each group were submitted for sterility and pyrogen testing.

Figure 7:
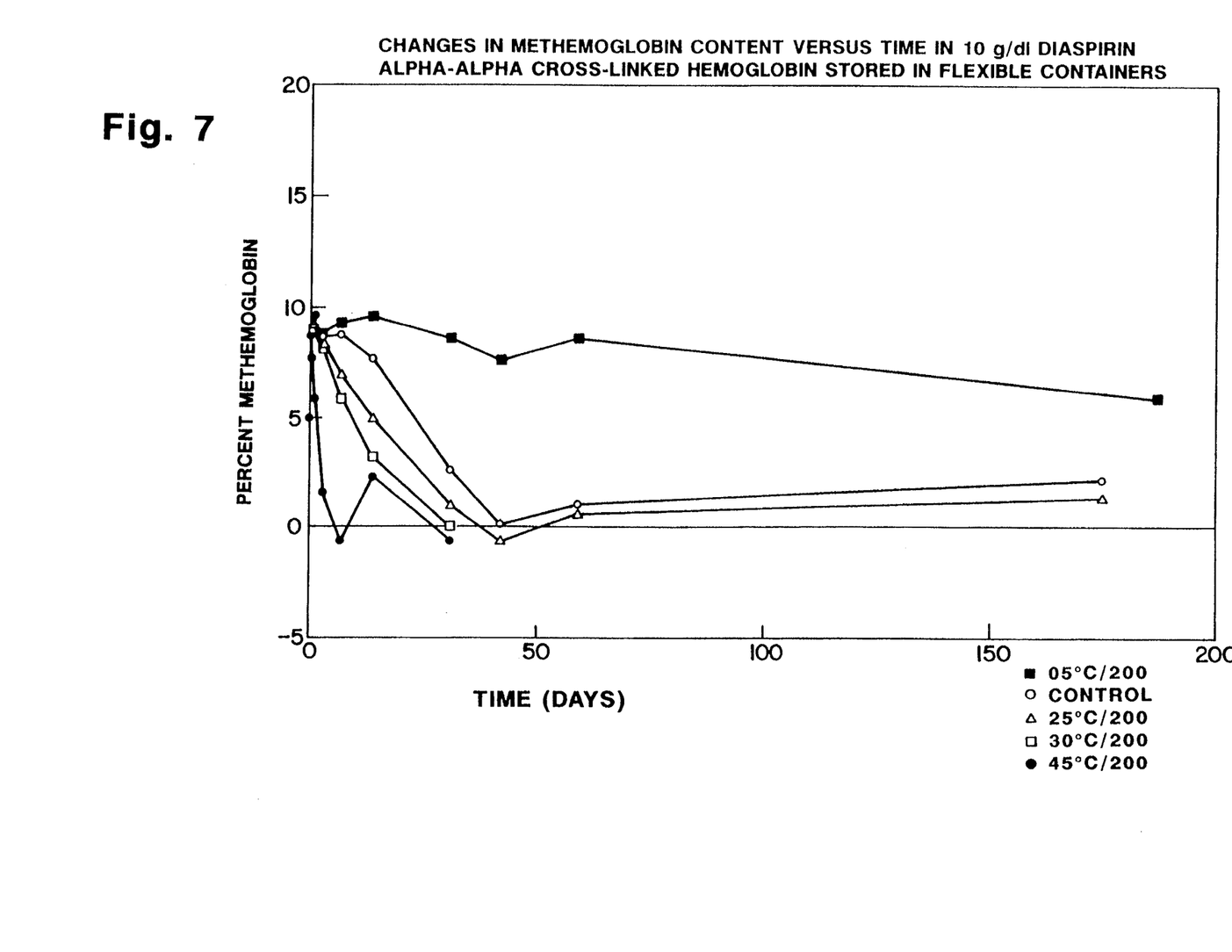
FIG. 7 shows the changes in percent methemoglobin versus time in a deoxygenated solution of 10 g/dl diaspirin cross-linked hemoglobin in lactated Ringer's. The packaging of the solution was carried out as in Example 6 above. Test group units contained a 200 ml capacity oxygen absorbing packet in the foil pouch and were stored at 5° C., 25° C., 30° C., or 45° C. Control group unit storage at 25° C. was without oxygen packets. Units in all groups were stored at 25° C.

The data from this experiment are given in Table 7 and FIG. 7. Results at 25° C. were similar to those obtained in Examples 5 and 6. The 45° C. response was particularly notable since the oxidative deoxygenation phase required less than a day to complete before the onset of autoreduction. All samples submitted were found to be sterile in aerobic and anaerobic culture and nonpyrogenic

TABLE 7

Changes in Percent Methemoglobin Content in a Solution of 10 g/dl Diaspirin Cross-Linked Hemoglobin in Lactated Ringer's Packaged in Flexible Containers

| | PERCENT METHEMOGLOBIN Temp: | | | | |
|---|---|---|---|---|---|
| | 25° C. | 5° C. | 25° C. | 30° C. | 45° C. |
| TIME/ | | | # Packets: | | |
| DAYS | 0 | 1 | 1 | 1 | 1 |
| PRE* | 5.0 | 5.0 | 5.0 | 5.0 | 5.0 |
| POST** | 7.7 | 7.7 | 7.7 | 7.7 | 7.7 |
| 1 | 9.7 | 9.2 | 9.2 | 9.0 | 5.9 |
| 3 | 8.7 | 8.9 | 8.4 | 8.1 | 1.6 |
| 7 | 8.8 | 9.3 | 7.0 | 5.9 | ND |
| 14 | 7.7 | 9.6 | 5.0 | 3.2 | 2.3 |
| 31 | 2.6 | 8.6 | 1.0 | 0 | ND |
| 42 | 0.1 | 7.6 | ND | NS | NS |
| 59*** | 1.0 | 8.6 | 0.6 | NS | NS |
| 175 | 2.0 | NS | 1.2 | NS | NS |
| 187 | NS | 5.8 | NS | NS | NS |

TABLE 7-continued

Changes in Percent Methemoglobin Content in a Solution of 10 g/dl Diaspirin Cross-Linked Hemoglobin in Lactated Ringer's Packaged in Flexible Containers

| TIME/ | PERCENT METHEMOGLOBIN Temp: | | | | |
|---|---|---|---|---|---|
| | 25° C. | 5° C. | 25° C. | 30° C. | 45° C. |
| | # Packets: | | | | |
| DAYS | 0 | 1 | 1 | 1 | 1 |
| 231 | 0.6 | NS | 0.6 | NS | NS |

PRE* = preprocessing; the level of methemoglobin before deoxygenation and packaging.
POST** = post-processing; the level of methemoglobin after deoxygenation and packaging were completed.
*** = measurements to determine hemoglobin moieties collected on a Cary 2200 from day 59 to the end of study. Previous measurements were from a Hewlett-Packard 8451A instrument.
ND = not detected.
NS = not sampled.

EXAMPLE 8

In this experiment we evaluated whether inclusion of oxygen absorbing packets in overpouch may be beneficial over a long storage interval. The test groups in this experiment contained one, two or four type S-200 Ageless (Mitsubishi Chemical Co.) packets in the package head space corresponding to 200, 400 or 800 ml of oxygen absorbing capacity, respectively. Once again, a 10 g/dl solution of diaspirin cross-linked hemoglobin in lactated Ringer's was packaged in flexible containers and foil pouches using the isolator technology described in Example 5 and the more rigorous steps to exclude oxygen described in Example 6. The study was designed for a one year duration.

Figure 8:
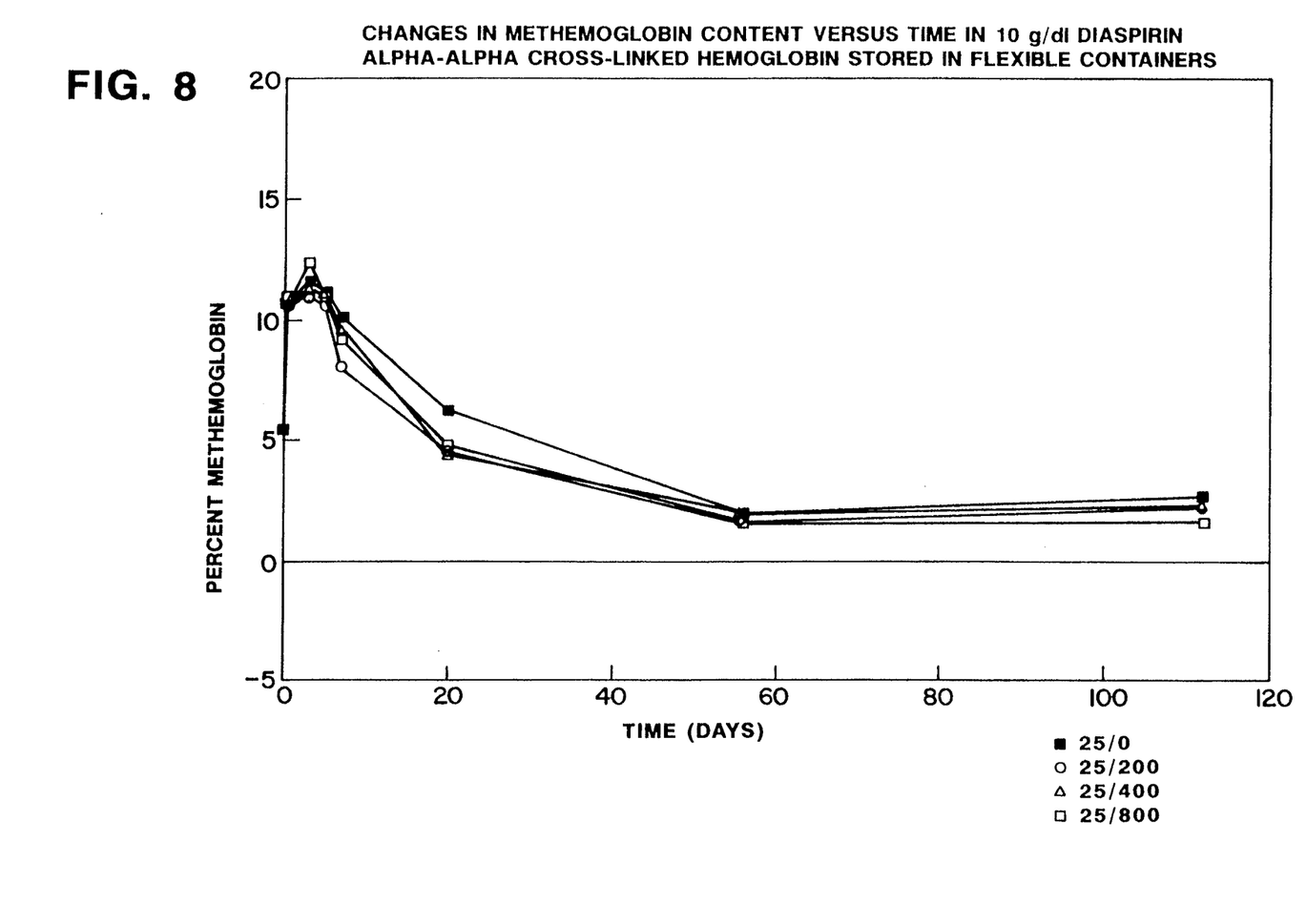
FIG. 8 shows the changes in percent methemoglobin versus time in a deoxygenated solution of 10 g/dl diaspirin cross-linked hemoglobin in lactated Ringer's. Test group units contained 200, 400 or 800 ml of oxygen absorbing capacity while the control group units contained no packets.

There may have been a small effect on the rate of autoreduction comparing control group sample with samples containing oxygen absorbing packets, but essentially all groups displayed virtually identical autoxidation-autoreduction behavior (Table 8; FIG. 8).

TABLE 8

Changes in Percent Methemoglobin Content In a Solution of 10 g/dl Diaspirin Cross-Linked Hemoglobin in Lactated Ringer's Packaged in Flexible Containers

| TIME/ | PERCENT METHEMOGLOBIN Temp: | | | |
|---|---|---|---|---|
| | 25° C. | 25° C. | 25° C. | 25° C. |
| | # Packets: | | | |
| DAYS | 0 | 1 | 2 | 4 |
| PRE* | 5.4 | 5.4 | 5.4 | 5.4 |
| POST** | 10.8 | 10.8 | 10.8 | 10.8 |
| 3 | 11.6 | 11.0 | 11.3 | 12.4 |
| 5 | 11.2 | 10.6 | 11.1 | 11.0 |
| 7 | 10.1 | 8.1 | 9.6 | 9.2 |
| 20 | 6.2 | 4.5 | 4.4 | 4.7 |
| 56 | 1.9 | 1.5 | 1.9 | 1.6 |
| 112 | 2.5 | 2.1 | 2.2 | 1.5 |

TABLE 8-continued

Changes in Percent Methemoglobin Content In a Solution of 10 g/dl Diaspirin Cross-Linked Hemoglobin in Lactated Ringer's Packaged in Flexible Containers

| TIME/ | PERCENT METHEMOGLOBIN Temp: | | | |
|---|---|---|---|---|
| | 25° C. | 25° C. | 25° C. | 25° C. |
| | # Packets: | | | |
| DAYS | 0 | 1 | 2 | 4 |
| 168 | 1.5 | 1.2 | 1.8 | 1.2 |

PRE* = preprocessing; the level of methemoglobin before deoxygenation and packaging.
POST** = post-processing; the level of methemoglobin after deoxygenation and packaging were completed.

Samples from examples 7 and 8 were assayed for enzymes known to protect hemoglobin against oxidative damage. See Table 9.

TABLE 9

Activities[2] of Reductive Enzymes per Gram of Hemoglobin

| TYPE OF HEMO-GLOBIN | HEMO-GLOBIN (g/100 mL) | GLUTATHIONE REDUCTASE | | METH-EMO-GLOBIN REDUC-TASE |
|---|---|---|---|---|
| | | No FAD | With FAD | |
| Human Erythrocytes | | 7.18 | 10.4 | 19.21 |
| Human Hemolysate | 1.03 | | | 13.61 |
| DeoxyDCLHb | 9.97 | 0.35 | 0.56 | Not Detected |
| DeoxyDCLHb | 9.72 | 1.58 | 0.04 | Not Detected |

[2]Activity is defined on the basis that one unit of enzyme catalyzes the conversion of 1μ mole of substrate per minute. In ancillary studies of parallel samples of diaspirin cross-linked hemoglobin, it has been shown that NADH-methemoglobin reductase, catalase, and superoxide dismutase activities could not be detected.

The absence of normal reductive enzymatic activity in these samples confirms that autoreduction of hemoglobin under the conditions described in this Invention is independent of enzyme systems present in unpurified samples.

Although, the invention has been shown in connection with certain specific embodiments, it will be readily apparent to those skilled in the art that various changes in form and arrangement of steps can be made to suit requirements without departing from the spirit and scope of the invention.

We claim:

1. A system for storing hemoglobin at a temperature of −270 to 45 degrees Centigrade comprising
    a stable thoroughly deoxygenated hemoglobin solution having a methemoglobin content of less than fifteen percent, and
    a nitrogen-purged oxygen impermeable container containing said hemoglobin.

2. A method for storing hemoglobin comprising
    purging an oxygen impermeable container with nitrogen,
    thoroughly deoxygenating a purified hemoglobin solution to be stored,
    filling the said oxygen impermeable container with aliquots of said purified hemoglobin solution,
    sealing said containers,
    scavenging residual oxygen from said hemoglobin solution during an oxygen scavenging phase,
    storing said containers at 5 degrees to 45 degrees Centigrade to permit autoreduction of methemoglobin to levels of less than fifteen percent, and
    further storing said hemoglobin solution at between −270 and 45 degrees Centigrade.

* * * * *